US00PP18592P3

(12) United States Plant Patent
Collinge

(10) Patent No.: US PP18,592 P3
(45) Date of Patent: Mar. 11, 2008

(54) APPLE VARIETY NAMED 'CJ07'

(50) Latin Name: *Malus domestica*
Varietal Denomination: CJ07

(75) Inventor: Peter Collinge, Napier (NZ)

(73) Assignee: The Horticulture and Food Research Institute of New Zealand Ltd., Palmerston North (NZ)

( * ) Notice: Subject to any disclaimer, the term of this patent is extended or adjusted under 35 U.S.C. 154(b) by 1012 days.

(21) Appl. No.: 10/032,692

(22) Filed: Dec. 27, 2001

(65) Prior Publication Data

US 2003/0167547 P1 Sep. 4, 2003

(51) Int. Cl.
*A01H 5/00* (2006.01)

(52) U.S. Cl. ..... Plt./161
(58) Field of Classification Search ..... Plt./161
See application file for complete search history.

(56) References Cited

U.S. PATENT DOCUMENTS

PP5,584 P * 12/1985 Dayton et al. ..... Plt./161
PP7,956 P * 9/1992 Alston ..... Plt./161

OTHER PUBLICATIONS

UPOV–International Union for the Protection of New Varieties of Plants; Guidelines for the Conduct of Tests for Distinctness, Uniformity and Stability; Apple; Apr. 6, 2005; 45 pages.*

* cited by examiner

*Primary Examiner*—Kent Bell
*Assistant Examiner*—S. B. McCormick-Ewoldt
(74) *Attorney, Agent, or Firm*—Stratton Ballew PLLC

(57) ABSTRACT

A new and distinct apple variety is described. The variety results from a whole tree mutation of the variety 'Sciearly' (PP11,092). The fruit of the apple tree of this new variety has an attractive appearance characterized by intense red block colour, early harvest maturity, and large fruit size relative to other early season cultivars. The new variety is known by the denomination 'CJ07'.

4 Drawing Sheets

Latin name of the genus and species: *Malus domestica.* Variety denomination: 'CJ07'.

BACKGROUND AND SUMMARY OF THE INVENTION

The present invention relates to a new and distinct apple variety named 'CJ07'. The new variety was discovered in January 1996 as a whole tree mutation of 'Sciearly' (PP11,092), growing in a block of 'Sciearly' trees in the discoverer's orchard in Hawkes Bay, New Zealand. The 'Sciearly' trees were growing on MM106 rootstock and had been established on the orchard as part of the original release of the 'Sciearly' variety in New Zealand.

'CJ07' was originally noted to its early development of bright red fruit colour. All fruit on the tree appeared to be consistently ahead in colour development than fruit on surrounding 'Sciearly' trees obtained from the same original source. The colour development was particularly notable considering the parent variety was selected for its early harvest season and dark red block colour.

Budwood was taken from the original tree at the time of discovery and 140 trees were propagated on MM106 rootstock, and 100 trees on M793 rootstock. These trees were planted on the discoverer's orchard property in winter 1997 and produced their first crop in January 1999. The colour and harvest maturity period of fruit on these trees was found to be consistent with the original tree, and true to type.

A further generation of trees was produced and was established in the discoverer's orchard in winter 1998. Fruit from these trees have exhibited the early fruit colour development and typical red colour of the original mutation over three seasons.

The new variety was determined to be distinct in comparison with the parent variety 'Sciearly' by the following characteristics:

- fruit colour at harvest maturity which is a brighter, more intense red.
- an earlier harvest season by at least a week, determined on the basis of background colour development.

BRIEF DESCRIPTION OF PHOTOGRAPHS

The accompanying photographs show typical specimens of the young tree, flowers, foliage and fruit of the new variety as depicted in colours as nearly true as is reasonably possible to make the same in a colour illustration of this character.

DETAILED BOTANICAL DESCRIPTION OF THE VARIETY

Figure 1:
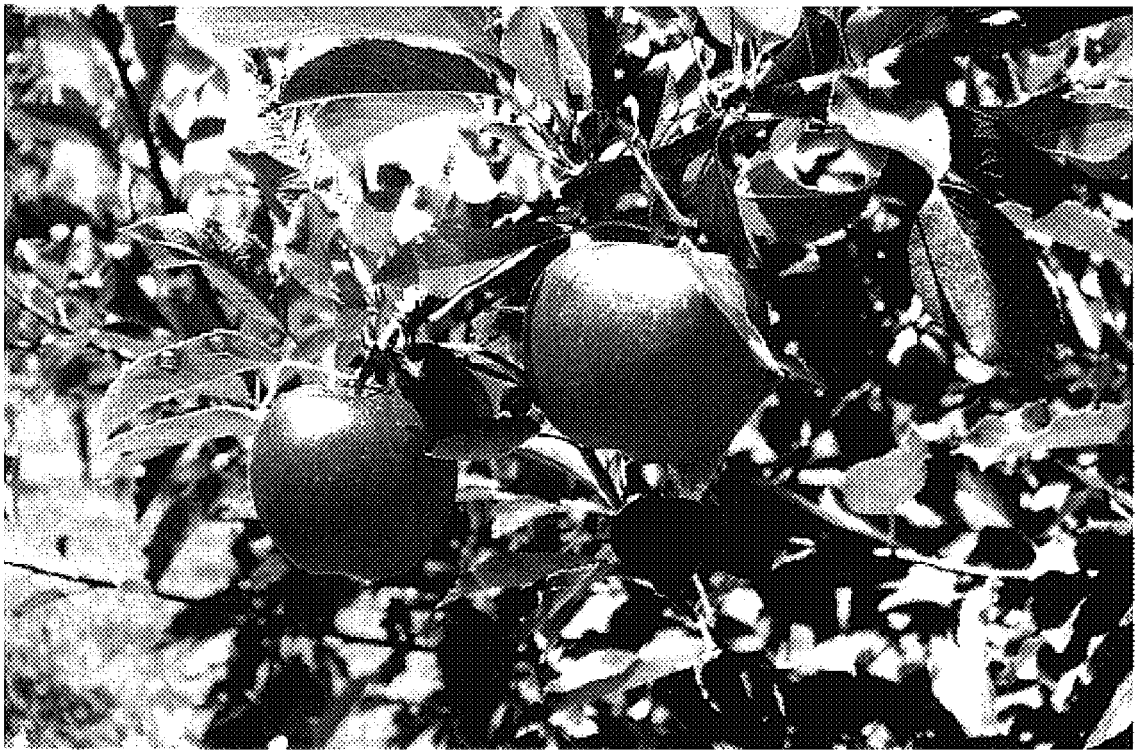
FIG. 1 shows a typical fruit of the apple variety 'CJ07' photographed in situ on the original tree of the whole tree mutation.
Figure 2:
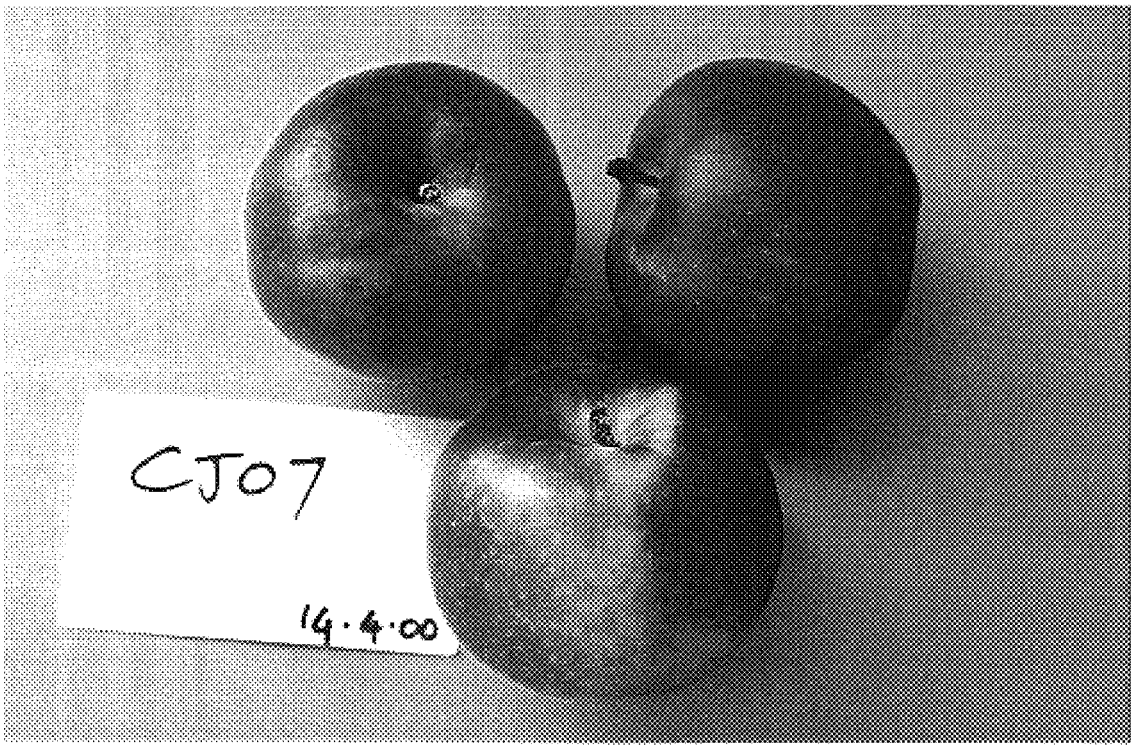
FIG. 2 shows stem end and side views, showing both blush and shade sides, of a typical fruit of the apple variety 'CJ07'. The fruit shown in FIG. 2 was obtained from trees asexually propagated from the original whole tree mutation.
Figure 3:
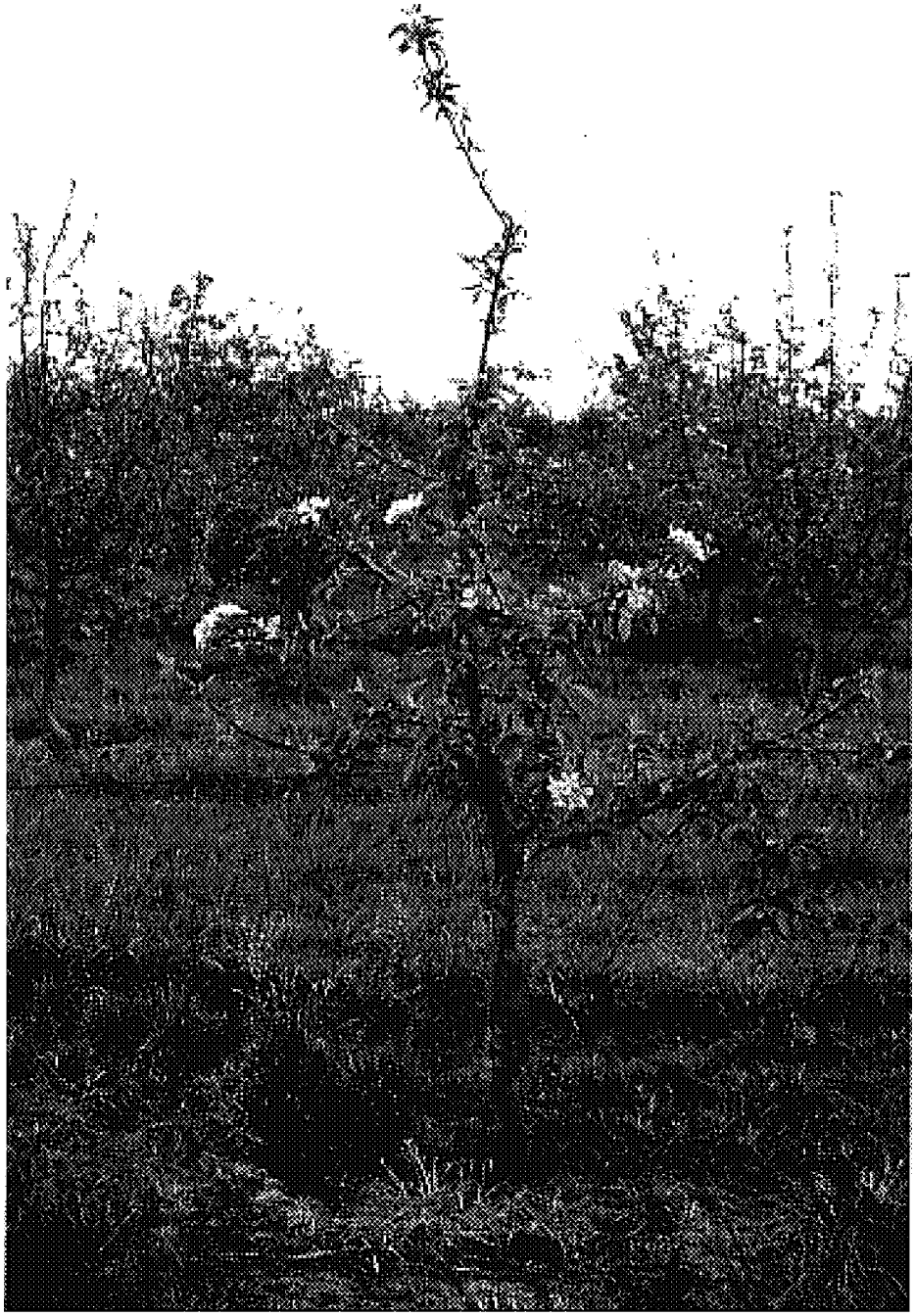
FIG. 3 shows a young tree ($3^{rd}$ leaf in the orchard) showing foliage and typical branching development.
Figure 4:
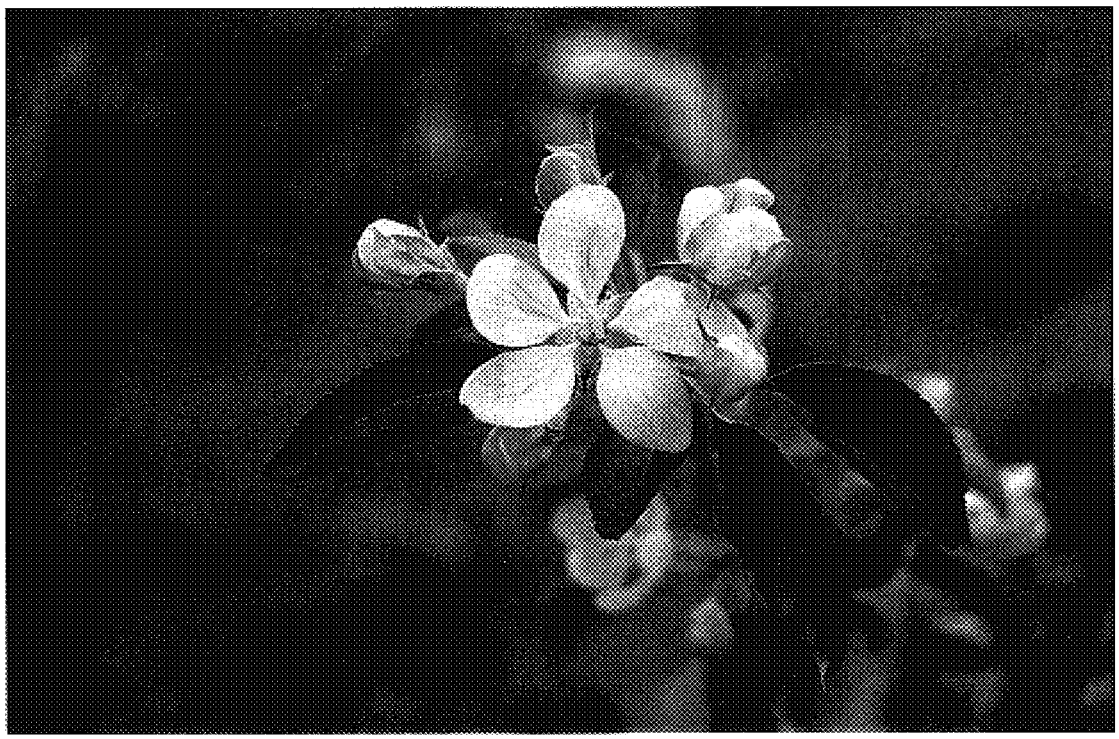
FIG. 4 shows typical flower and foliage of the variety 'CJ07'.

The following is a detailed description of the new variety with colour terminology in accordance with The Royal Horticultural Society Colour Chart (RHSCC) 2001 edition.

The specimens described were grown at the discoverer's property at 1999 Pakowhai Road, RD3, Napier, New Zealand. The observations were made in the 2000-2001 season on trees on MM. 106 rootstock that were four years old at the time, and managed under standard orchard practice. It should be understood that the characteristics described will vary depending upon cultural practices, climatic conditions, planting location and season.

Tree: Medium size; spreading habit; height approximately 3 m, width approximately 2 m; bearing on both one-year wood and spurs; medium vigour on MM.106 rootstock.

Trunk: Moderately rough; circumference 240 mm at a height of 200 mm; the bark is grey-green RHSCC 197C when mature.

Branches: Bark moderately rough, grey-green RHSCC 197C when mature; moderate branching, in a whorl arrangement, the angle of branching being typically 20 degrees above the horizontal; approximately 5 spurs per 100 mm of growth on two year old wood; length of annual growth 300–350 mm (measured on extension shoots arising from branches arising approximately 1.5 m above ground level); lenticels round, greyed-orange 165D, approximately 1 mm diameter, 8 per $cm^2$.

Lenticels: Medium size; average numbers.

Leaves: Average length 106 mm; average width 53 mm; upward pose; upfolded to concave shape in cross section; serrate indentation of margin; medium glossiness on upper surface; weak pubescence on lower side; petiole length 30–45 mm; small to insignificant stipule size; colour of blade is green RHSCC 137A.

Flowers: Medium blooming period, starting about 5 October for 2 weeks; medium size, diameter approximately 5 cm; five petals, margin of petals not touching; bud colour pink RHSCC 55B fading to white as the flower opens; five sepals small size, pointed, green with red tips; pubescent ovary; 5 to 6 flowers per cluster; not self-fertile, pollinator required.

Fruit: Examined at optimum. The main harvest period typically is from about 11 February until 25 February in Hawkes Bay, New Zealand.

Size: Large to very large; average width, 76 mm; average height, 62 mm; average weight, 200 g.

Shape: Short globose, conical; symmetrical in side view; ribbing absent; medium degree of crowning at distal end.

Cavity: Average width, 36 mm; average depth, 12 mm.

Basin: Average width, 28 mm; average depth, 9 mm.

Stem: Medium thickness; medium length, 24 mm.

Sepal: Medium length; spacing, touching.

Eye: Size, medium; aperture, closed.

Skin: Smooth; bloom of skin, absent; greasiness of skin, slight, cracking tendency of skin, absent; thickness, medium; background colour, yellow-green RHSCC 145C; lenticels, small, round to oval, diameter 1 to 2 mm, yellow-green RHSCC 145C.

Over Colour: Approximately 80% of skin surface; bright red, RHSCC 46B; some russet around stem end cavity.

Flesh: Medium first, juicy and crisp; tinged light yellow RHSCC 10D.

Flavour: Sweet; medium acidity; mild aroma.

Quality: Excellent.

Sinus: Closed.

Seeds: Five locules; 1 to 2 seeds per locule; 8–10 seeds total; medium size, average 10 mm long and 5 mm wide; colour, brown RHSCC 175A.

Use: Dessert.

Keeping quality: Excellent.

Production: Early season, regular cropping, although slight tendency to biennial variation in production volume.

Management: Thinning of the crop load in early summer is recommended and tailoring pruning to account for the slight biennial tendency.

We claim:

1. A new and distinct apple tree, substantially as shown and described herein.

* * * * *